United States Patent
Karanam et al.

(10) Patent No.: US 11,948,250 B2
(45) Date of Patent: Apr. 2, 2024

(54) MULTI-VIEW PATIENT MODEL CONSTRUCTION

(71) Applicant: Shanghai United Imaging Intelligence Co., Ltd., Shanghai (CN)

(72) Inventors: Srikrishna Karanam, Brighton, MA (US); Meng Zheng, Cambridge, MA (US); Ziyan Wu, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 62 days.

(21) Appl. No.: 17/513,534

(22) Filed: Oct. 28, 2021

(65) Prior Publication Data

US 2023/0140003 A1    May 4, 2023

(51) Int. Cl.
| | |
|---|---|
| *G06T 17/20* | (2006.01) |
| *A61B 34/10* | (2016.01) |
| *A61B 90/00* | (2016.01) |
| *G06T 7/70* | (2017.01) |

(52) U.S. Cl.
CPC .............. *G06T 17/20* (2013.01); *A61B 34/10* (2016.02); *A61B 90/361* (2016.02); *G06T 7/70* (2017.01); *A61B 2034/105* (2016.02); *A61B 2034/107* (2016.02); *A61B 2090/367* (2016.02); *G06T 2207/30196* (2013.01)

(58) Field of Classification Search
CPC . G06T 17/20; G06T 7/70; G06T 2207/30196; A61B 5/0035; A61B 2034/105
USPC ........................................................ 345/419
See application file for complete search history.

(56) References Cited

U.S. PATENT DOCUMENTS

| 10,311,648 | B2* | 6/2019 | Murali ................. H04N 13/239 |
| 10,546,417 | B2* | 1/2020 | Black ................... G06V 40/103 |
| 11,147,627 | B2* | 10/2021 | Gangwar ................ G06T 19/20 |
| 2008/0159608 | A1* | 7/2008 | Suetens .................. A61B 34/10 |
| | | | 382/128 |
| 2013/0166256 | A1* | 6/2013 | Wirx-Speetjens ..... B33Y 50/00 |
| | | | 703/1 |
| 2016/0148435 | A1* | 5/2016 | Li .......................... G06F 3/0482 |
| | | | 715/848 |
| 2016/0151696 | A1* | 6/2016 | Chen .................. A63B 24/0006 |
| | | | 473/199 |
| 2020/0098177 | A1* | 3/2020 | Ni .............................. G06T 7/50 |
| 2020/0210692 | A1* | 7/2020 | Asayama ............... G06V 40/23 |
| 2020/0268251 | A1* | 8/2020 | Hao ....................... A61B 5/055 |

(Continued)

*Primary Examiner* — Javid A Amini
(74) *Attorney, Agent, or Firm* — Zhong Law LLC

(57) ABSTRACT

Systems, methods, and instrumentalities are described herein for constructing a multi-view patient model (e.g., a 3D human mesh model) based on multiple single-view models of the patient. Each of the single-view models may be generated based on images captured by a sensing device and, dependent on the field of the view of the sensing device, may depict some keypoints of the patient's body with a higher accuracy and other keypoints of the patient's body with a lower accuracy. The multi-view patient model may be constructed using respective portions of the single-view models that correspond to accurately depicted keypoints. This way, a comprehensive and accurate depiction of the patient's body shape and pose may be obtained via the multi-view model even if some keypoints of the patient's body are blocked from a specific sensing device.

18 Claims, 5 Drawing Sheets

(56) References Cited

U.S. PATENT DOCUMENTS

2021/0077191 A1* 3/2021 Sabczynski ............. G06T 19/20
2021/0121244 A1* 4/2021 Innanje .................. G06T 7/97
2021/0158937 A1* 5/2021 Wu ........................ G06T 7/50
2022/0215625 A1* 7/2022 Xia ........................ G06T 7/30

* cited by examiner

MULTI-VIEW PATIENT MODEL CONSTRUCTION

BACKGROUND

Three-dimensional (3D) patient models that realistically reflect the patient's body shape and pose can be used in a variety of medical applications including patient positioning, treatment planning, surgical navigation, etc. For example, in radiation therapy and medical imaging, success often hinges upon the ability to place and maintain the patient in a desirable position so that the procedures may be performed with better accuracy and faster speed. Having knowledge (e.g., visual knowledge) about the patient's physical characteristics in these situations is therefore crucial to obtaining optimal outcome for the patient. Conventional human mesh recovery (HMR) systems and methods utilize single images of the patient and expect that the patient's body will be visible (e.g., unblocked) in those images. In reality, however, the patient's body may be occluded at least partially by medical equipment and/or clothing items (e.g., hospital gowns, covering sheets, etc.) and as a result the single view based HMR systems and methods may not be able to produce satisfactory results. New and/or improved patient modeling and mesh construction techniques that are capable of accurately estimating the patient's body information despite having one or more parts of the patient's body blocked are therefore highly desirable.

SUMMARY

Described herein are systems, methods, and instrumentalities associated with constructing a multi-view patient model (e.g., 3D human mesh model) based on multiple single-view models of the patient. An apparatus as described herein may comprise one or more processors configured to obtain first information associated with a first 3D model (e.g., a first single-view model) of a human body and obtain second information associated with a second 3D model (e.g., a second single-view model) of the human body. The first 3D model may be determined based on at least a first image of the human body captured by a first sensing device (e.g., a first camera). The second 3D model may be determined based on at least a second image of the human body captured by a second sensing device (e.g., a second camera). The first information may indicate that the first 3D model covers (e.g., depicts with a high accuracy) at least a first keypoint (e.g., a first part such as the left shoulder) of the human body, and the second information may indicate that the second 3D model covers at least a second keypoint (e.g., a second part such as the right shoulder) of the human body. The one or more processors of the apparatus may be further configured to determine a first region (e.g., a first cuboid) of the first 3D model that is associated with the first keypoint and a second region (e.g., a second cuboid) of the second 3D model that is associated with the second keypoint, and generate a third 3D model (e.g., a multi-view 3D model) of the human body based on at least the first region of the first 3D model and the second region of the second 3D model.

In examples, the one or more processors may be configured to determine, based on the first 3D model, a first set of vertices associated with the first region of the first 3D model and determine, based on the second 3D model, a second set of vertices associated with the second region of the second 3D model, wherein the third 3D model of the human body is generated based on at least the first set of vertices and the second set of vertices. In examples, the one or more processors may be further configured to determine respective locations of the first set of vertices and the second set of vertices in a coordinate system associated with the third 3D model, and generate the third 3D model based on at least the respective locations of the first set of vertices and the second set of vertices in the coordinate system associated with the third 3D model. The respective locations of the first set of vertices and the second set of vertices in the coordinate system may be determined, for example, based on the respective positions of the first sensing device and the second sensing device in the coordinate system.

In examples, the one or more processors may be further configured to determine, based on the first information and the second information, that both the first 3D model and the second 3D model cover the second keypoint of the human body and determine, based on a confidence indication associated with at least one of the first 3D model or the second 3D model with respect to the second keypoint, that the second 3D model is to be used to obtain information associated with the second keypoint. The confidence indication may be determined, for example, based on a position of the first sensing device relative to the second keypoint and a position of the second sensing device relative to the second keypoint.

In examples, the first and second 3D models described herein may be constructed by the first sensing device and the second sensing device, respectively, and the apparatus may be configured to receive the first 3D model from the first sensing device and the second 3D model from the second sensing device. In examples, the apparatus may include the first sensing device or the second device, and may be configured to construct the first or second 3D model in addition to the third 3D model.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1:
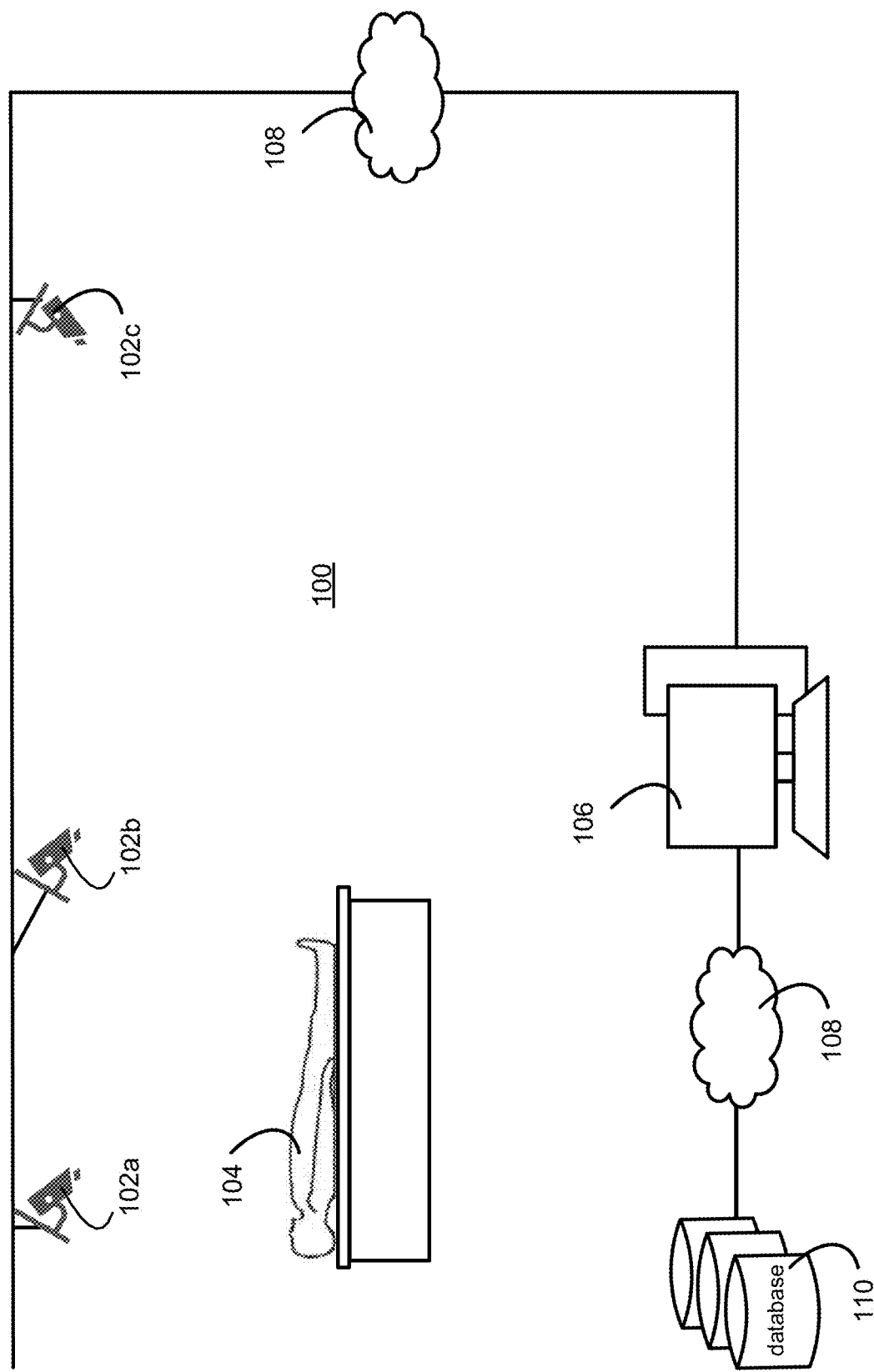
FIG. 1 is a simplified block diagram illustrating an example environment associated with one or more of the embodiments described herein.

FIG. 1 is a diagram illustrating an example environment 100 associated with one or more of the embodiments described herein. The environment 100 may be part of a medical facility such as a scan room (e.g., magnetic resonance imaging (MRI), X-ray, Computed Tomography (CT), etc.) or an operating room (OR), a rehabilitation facility, a fitness center, etc. The environment 100 may be equipped with one or more sensing devices (e.g., 102a, 102b, 102c) such as one or more digital cameras configured to capture images (e.g., two-dimensional (2D) images) of a patient 104 inside the environment 100. The sensing devices 102a-c may be communicatively coupled to a processing device 106 and/or other devices of the environment 100 via a communication network 108. Each of the sensing devices 102a-c may include one or more sensors such as one or more 2D visual sensors (e.g., 2D cameras), one or more 3D visual sensors (e.g., 3D cameras), one or more red, green, and blue (RGB) sensors, one or more depth sensors, one or more RGB plus depth (RGB-D) sensors, one or more thermal sensors (e.g., infrared (FIR) or near-infrared (NIR) sensors), one or more radar sensors, and/or other types of image capturing devices or circuitries.

While inside the environment 100, the body of the patient 104 may be blocked (e.g., partially blocked) by other equipment or items (e.g., the C-arm of an X-ray machine, a covering sheet, etc.) from the field of view (FOV) of a sensing device. For example, depending on the installation locations of the sensing devices 102a-c, the position and/or pose of the patient 104, and/or the locations of other equipment or items in the environment 100, the FOV of a first sensing device (e.g., 102a) may include a first set of regions or areas of the patient's body (e.g., left shoulder, left arm, etc.) and the FOV of a second sensing device (e.g., 102b) may include a second set of regions or areas of the patient's body (e.g., right shoulder, right arm, etc.). As a result, the first set of regions or areas may be visible in the images captured by the first sensing device but not in the images captured by the second sensing device. Likewise, the second set of regions or areas may be visible in the images captured by the second sensing device but not in the images captured by the first sensing device.

Each of the sensing devices 102a-c may include a functional unit (e.g., a processor) configured to process the images captured by the sensing device and generate (e.g., construct) a human model such as a 3D human mesh model for the patient based on the images. Such a human model may be referred to herein as a single-view model (e.g., since the model may be based on the field of view of one sensing device) and may include a plurality of parameters indicating the body shape and/or pose of the patient during a medical procedure (e.g., an MRI, X-ray, or CT procedure). For example, the parameters of the human model may be used to determine multiple vertices (e.g., 6890 vertices based on 82 shape and pose parameters) associated with the patient's body and each of the vertices may include respective position, normal, texture, and/or shading information. Using these vertices, a 3D mesh of the patient may be created, for example, by connecting multiple vertices with edges to form a polygon (e.g., a triangle), connecting multiple polygons to form a surface, using multiple surfaces to determine a 3D shape, and applying texture and/or shading to the surface and/or the shape.

The single-view models described herein may also be generated by the processing unit 106. For example, the processing unit 106 may be communicatively coupled to the sensing devices 102a-c and may receive images of the patient captured by the sensing devices (e.g., in real time or based on a predetermined schedule). Using the respective images received from each of the sensing devices, the processing unit 106 may build a corresponding single-view model for the patient that reflects the field of view of the sensing device. Similarly, the single-view models described herein may also be generated by one of the sensing devices based on images captured by another sensing device. For example, the sensing devices 102a-c may be inter-connected via the communication link 108 and exchange images with each other. One of the sensing devices may be configured to perform processing tasks (e.g., constructing the single-view models described herein) for the other sensing device(s) based on images received from the other sensing device(s).

Any of the sensing devices 102a-c and/or the processing unit 106 may be further configured to generate (e.g., construct) a multi-view model (e.g., a multi-view 3D human mesh model) for a patient based on multiple single-view models (e.g., the single-view models described herein) constructed for the patient. As described herein, each of these single-view models may correspond to a respective sensing device and may represent the body shape and/or pose of the patient from the field of view of the sensing device. Since the field of view of one sensing device may be different than that of another sensing device, the single-view models associated with different sensing devices may have different degrees of accuracy with respect to different regions or areas of the patient's body. For example, a first single-view model of the patient that is associated with a first sensing device may have a higher degree of accuracy with respect to the left side of the patient's body than the right side of the patient's body because the right side of the patient's body is blocked or obscured in the FOV of the first sensing device. On the other hand, a second single-view model of the patient that is associated with a second sensing device may have a higher degree of accuracy with respect to the right side of the patient's body than the left side of the patient's body because the left side of the patient's body is blocked or obscured in the FOV of the second sensing device. Accordingly, a multi-view model of the patient may be derived based on multiple (e.g., two or more) single-view models. In the scenario describe above, for example, a multi-view model may be derived by combining a portion of the first single-view model (e.g., corresponding to the left side of the patient's body) with a portion of the second single-view model (e.g., corresponding to the right side of the patient's body) such that the derived multi-view model may have a high degree of accuracy with respect to both sides of the patient's body. Techniques for constructing such a multi-view model will be described in greater detail below and are not limited to two single-view models (e.g., the description relating to two single-view models may also be applicable to three or more single-view models).

The models (e.g., single-view models and/or multi-view models) generated by the sensing devices 102a-c and/or the processing unit 106 may be used in a variety of clinical applications including, for example, patient positioning (e.g., during a scan or treatment procedure), medical equipment control (e.g., automatically adjusting the height of a scanner bed or operating table based the patient's body shape), unified medical record review (e.g., aligning scans from different imaging modalities on the same patient model), etc. The models may be provided to downstream applications or devices in real time or they may be saved to a repository (e.g., database 110) that is communicatively coupled to the sensing devices 102a-c and/or the processing unit 106 for later use.

Figure 2:
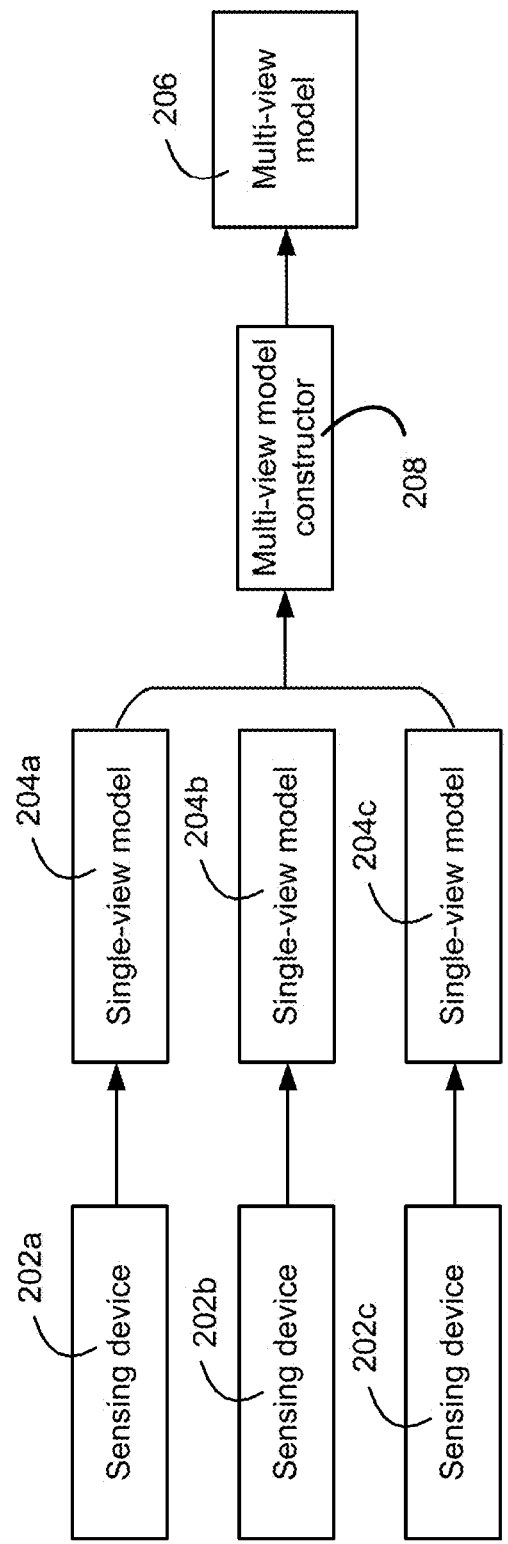
FIG. 2 is a simplified block diagram illustrating an example of generating a multi-view human model based on multiple single-view models.

FIG. 2 shows a diagram illustrating an example of generating a multi-view human model 206 based on multiple single-view models (e.g., 204a, 204b, 204c, etc.). The single-view models 204a-c are shown in this example as being generated by sensing devices 202a, 202b, 202c (e.g., the sensing devices 102a-c shown in FIG. 1) respectively. It should be noted, however, that one or more (e.g., all) of the single-view models 204a-c may also be generated by other device(s) such as the processing unit 106 described above or any one of the sensing devices 202a-c, so the description below may also be applicable to those other devices.

Using sensing device 202a as an example, the sensing device may be configured to capture images (e.g., 2D images) of a patient that reflect the sensing device's field of view of the patient. The sensing device 202a may be further configured to generate a human model 204a (e.g., a 3D human mesh model) based on one or more of the images captured by the sensing device. The sensing device 202a may accomplish the task, for example, using a pre-trained artificial neural network (ANN) such as an autoencoder. The ANN may be trained to extract features from the images captured by the sensing device 202a and infer (e.g., estimate or predict) parameters from the extracted features for recovering the human model. The inferred parameters may include, for example, one or more pose parameters, $\Theta$, and one or more shape parameters, $\beta$, which may respectively indicate the pose and shape of the patient's body. The ANN may comprise multiple layers such as an input layer, one or more convolutional layers, one or more pooling layers, one or more fully connected layers, and/or an output layer. Each of the layers may correspond to a plurality of filters (e.g., kernels) and each filter may be designed to detect (e.g., learn) a respective feature or pattern present in the input image. The filters may be associated with respective weights that, when applied to an input, produce an output indicating whether certain visual features or patterns have been detected. The weights associated with the filters may be learned by the ANN through a training process that may comprise inputting a large number of images from one or more training datasets to the ANN, calculating differences or losses (e.g., based on an objective function such as mean squared error or L1 norm, a margin based loss function, etc.) associated with a current prediction or estimate, and updating the weights assigned to the filters so as to minimize the differences or losses (e.g., based on a stochastic gradient descent of the loss function). Once trained, the ANN may take an image at the input layer, extract and/or classify visual features or patterns from the image, and provide an indication at the output layer regarding the presence of the identified features or patterns. The identified features may be indicated, for example, by a feature map or feature vector.

The ANN may also be trained to infer, e.g., based on features extracted from an input image, pose and shape parameters for recovering a 3D human model. For example, the ANN may be trained to determine, based training datasets that cover a wide range of human subjects, human activities, background noises, shape and/or pose variations, camera motions, etc., the joint angles of the patient as depicted in an image of the patient. The plurality of joints may include, for example, 23 joints comprised in a skeletal rig as well as a root joint, and the pose parameters derived thereof may include 72 parameters (e.g., 3 parameters for each of the 23 joints and 3 parameters for the root joint, with each parameter corresponding to an axis-angle rotation from a root orientation). The ANN may learn to determine, based on the training datasets, one or more shape parameters for predicting a blend shape of the patient based on the image of the patient. For example, the ANN may learn to determine the shape parameters by conducting a principal component analysis (PCA) of the image and the shape parameters thus determined may include a plurality of coefficients (e.g., the first 10 coefficients) of the PCA space. Once the pose and shape parameters are determined, a plurality of vertices (e.g., 6890 vertices based on 82 shape and pose parameters) may be obtained for constructing a model (e.g., a 3D mesh) of the patient's body. Each of the vertices may include respective position, normal, texture, and/or shading information. Using these vertices, a 3D mesh of the patient may be created, for example, by connecting multiple vertices with edges to form a polygon (e.g., such as a triangle), connecting multiple polygons to form a surface, using multiple surfaces to determine a 3D shape, and applying texture and/or shading to the surfaces and/or shapes.

As part of the model construction process described above, the sensing device 202a may determine a plurality of keypoints (e.g., 2D anatomical keypoints) of the patient's body that are visible in the image(s) captured by the sensing device and thus covered (e.g., depicted) by the human model 204a generated therefrom (e.g., with a high degree of accuracy and/or confidence). The keypoints (e.g., anatomical keypoints) may correspond to different regions or areas of the patient's body and may be determined based on the features extracted from the image(s). The keypoints captured by the sensing device and/or covered by the human model 204a (e.g., with a high level of accuracy and/or confidence) may also be determined based on the spatial relationships of the sensing device 202a, the patient, and/or other objects in the vicinity of the sensing device or the patient. For example, the keypoints that are captured by the sensing device (e.g., in the FOV of the sensing device) may be determined based on the installation location and/or angle of the sensing device 202a, and/or the location, height, and/or movement trajectory of one or more equipment that are blocking the sensing device's FOV of the patient. Such spatial information may be predetermined (e.g., during a device installation or calibration process) and used to determine (e.g., calculate) which keypoints of the patient's body may be visible in the image(s) captured by the sensing device 202a and thus may be covered by the human model 204a with a high degree of accuracy or confidence.

Accuracy or confidence indications such as accuracy or confidence scores may be determined and/or stored to indicate which keypoint(s) covered by a sensing device or a single-view model may have a higher level of accuracy or a higher confidence score (e.g., completely visible to the sensing device) and which keypoint(s) covered by a sensing device or a single-view model may have a lower level of accuracy or a lower confidence score (e.g., partially visible or invisible to the sensing device). Such accuracy or confidence indications may be determined by each sensing device, for example, during the process of analyzing the images captured by the sensing device and generating the single-viewing model as described herein. The accuracy or confidence indications may also be determined by a separate computing device such as the processing unit 106 of FIG. 1. The computing device may determine the accuracy or confidence indications for each keypoint and/or sensing device, for example, based on the spatial relationship between the sensing device and the patient. For example, the computing device may assign a low accuracy or confidence score to a specific keypoint/sensing device if the computing device determines that the keypoint is not in the FOV of the sensing device or partially blocked in the FOV of the sensing device. Conversely, the computing device may assign a high accuracy or confidence score to a specific keypoint/sensing device if the computing device determines that the keypoint is entirely in the FOV of the sensing device.

A multi-view model constructor 208 may be configured to receive information regarding all or a subset of the single-view human models 204a-c and construct the multi-view model 206 based on the received information. It should be noted that the multi-view model constructor 208 may be a compute device independent from the sensing devices 202*a*-*c* or the multi-view model constructor 208 may be one of the sensing devices 202*a*-*c*. So, the fact that the multi-view model constructor 208 is depicted in FIG. 2 as being separate from the sensing devices 202*a*-*c* should not be interpreting as indicating that the sensing devices 202*a*-*c* may not assume the role of the multi-view model constructor 208. In any event, the multi-view model constructor 208 may be configured to obtain (e.g., receive) respective information regarding two or more of the single-view models generated by the sensing device 202*a*-*c*, determine respective keypoint(s) (e.g., 2D keypoints) of the patient's body that may be covered (e.g., depicted) by each of the single-view models at a specific level of accuracy or confidence, and generate the multi-view model 206 using respective portions of the single-view models corresponding to those keypoints. For example, the multi-view model constructor 208 may receive first information associated with a first single-view model of the patient (e.g., model 204*a*) and second information associated with a second single-view model of the patient (e.g., model 204*b*). The first information may indicate that the first model covers (e.g., depicts) at least a first keypoint (e.g., left shoulder) of the patient's body (e.g., with a satisfactory level of accuracy or confidence) and the second information may indicate that the second model covers at least a second keypoint (e.g., left leg) of the patient's body (e.g., with the satisfactory level of accuracy or confidence). Based on the first and second information, the multi-view model constructor 208 may determine a first region of the first single-view model that is associated with the first keypoint and a second region of the second single-view model that is associated with the second keypoint, and generate the multi-view model 206 (e.g., a third model) based on at least the first region of the first single-view model and the second region of the second single-view model.

The multi-view model constructor 208 may determine and/or store the correlations between various keypoints (e.g., 2D keypoints) of the patient's body and regions (e.g., 3D regions) in each of the single-view models 204*a*-*c*. Such a region may include, for example, a set of vertices of the corresponding single-view model. For example, a region corresponding to a right shoulder keypoint may include a cuboid of certain dimensions that surrounds the right shoulder and encompasses a number of vertices of the single-view model. The regions (e.g., cuboids) and their dimensions may be pre-configured or predefined by or for the multi-view model constructor 208. Accordingly, the multi-view model constructor 208 may build the multi-view model 206 by iterating through a list of keypoints associated with the patient's body, selecting a region from the multiple single-view models (e.g., 204*a*-*c*) that corresponds to each of the keypoints, and use that region (e.g., vertices and/or model parameters associated with the region) to construct a part of the multi-view model 206. If multiple single-view models cover a keypoint with a certain level of accuracy or confidence (e.g., the right shoulder is visible in the FOV of both sensing devices 202*a* and 202*b*, and is covered by both single-view models 204*a* and 204*b*), the multi-view model constructor 208 may select a corresponding region from the single-view model that has the highest accuracy or confidence score for the keypoint (e.g., the right shoulder).

For each of the regions selected, the multi-view model constructor 208 may determine a set of vertices from the corresponding single-view model that may be used to build the multi-view model 206. In examples, the multi-view model constructor 208 may project the set of vertices (e.g., covert the locations of the vertices) from the coordinate system associated with the single-view model into a coordinate system associated with the multi-view model 206 (e.g., a "world" coordinate system). The "world" coordinate system may be defined in various ways, for example, based on the requirements of a downstream application. For instance, the "world" coordinate system may be defined based on the perspective of the multi-view model constructor 208, based on the perspective of a medical professional, based on the perspective of a display device used to present the multi-view model 206, etc. The projection (e.g., conversion) may be performed, for example, based on a respective camera-to-world rotation matrix and/or translation vector associated with each sensing device 202*a*, 202*b*, 202*c*. Such rotation matrix and/or translation vector may be determined (e.g., pre-determined during system calibration), for example, based on respective locations of the sensing devices relative to the "world" (e.g., an origin location of the "world" coordinate system).

Once the vertices corresponding to the different regions of the single-view models are converted (e.g., unified in the "world" coordinate system), the multi-view model constructor 208 may combine them and derive the multi-view model 206 based on the combination (e.g., by connecting the vertices with edges to form a polygon, connecting multiple polygons to form a surface, using multiple surfaces to determine a 3D shape, and/or applying texture and/or shading to the surfaces and/or shapes). This way, each sensing device's view of the patient (e.g., as reflected in each single-view model 204*a*, 204*b*, 204*c*) may be converted and combined to form a "world" view of the patient (e.g., as reflected in the multi-view model 206) that covers all keypoints of the patient's body.

Figure 3:
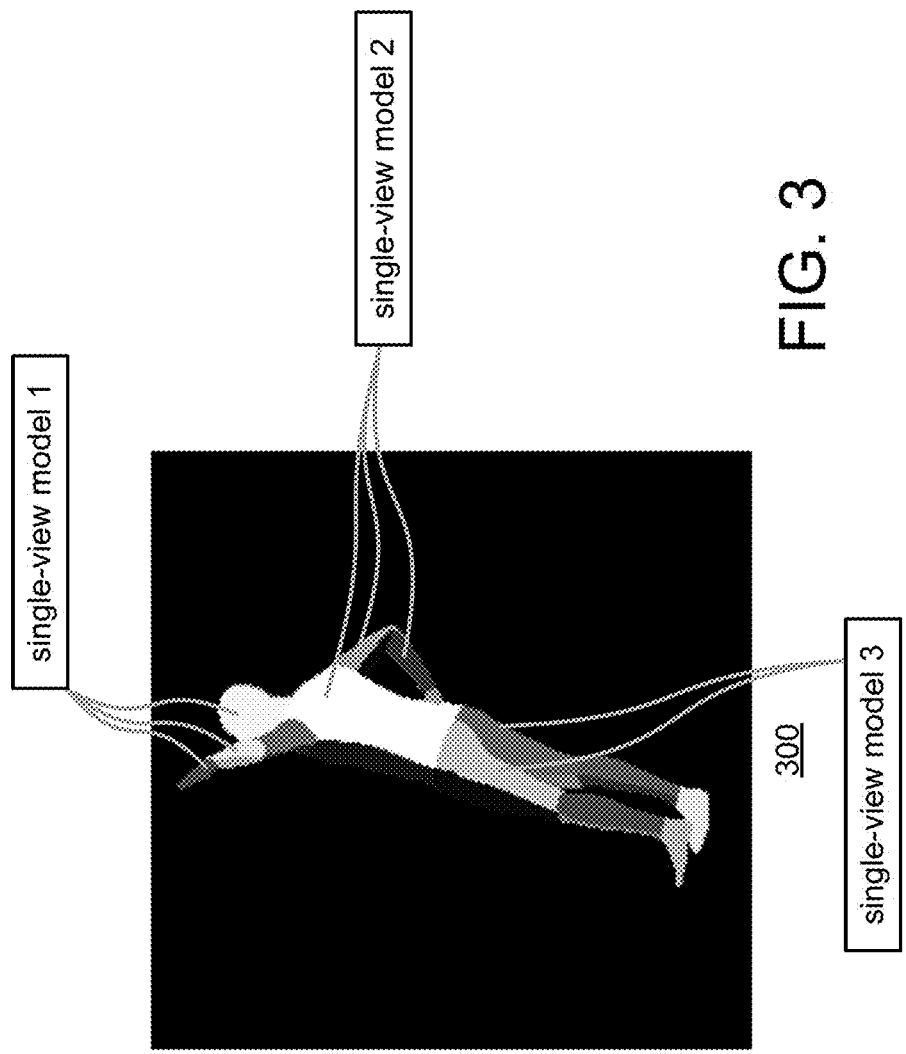
FIG. 3 is a simplified diagram illustrating the construction of a multi-view human model based on multiple single-view human models.

FIG. 3 shows a diagram illustrating the construction of a multi-view human model 300 (e.g., such as the multi-view model 206 in FIG. 2) based on multiple single-view human models (e.g., the single-view models 204*a*-*c* in FIG. 2). As shown, a first part of the multi-view human model 300 including the head and left arm may be constructed based on single-view model 1, for example, based on a determination that single-view model 1 covers those keypoints with a satisfactory level of accuracy or confidence (e.g., the level may be predefined). Similarly, a second part of the multi-view human model 300 including the back and right arm may be constructed based on single-view model 2, and a third part of the multi-view human model 300 including the left and right legs may be constructed based on single-view model 3, based on a determination that single-view models 2 and 3 cover the respective keypoints with the satisfactory level of accuracy or confidence.

Figure 4:
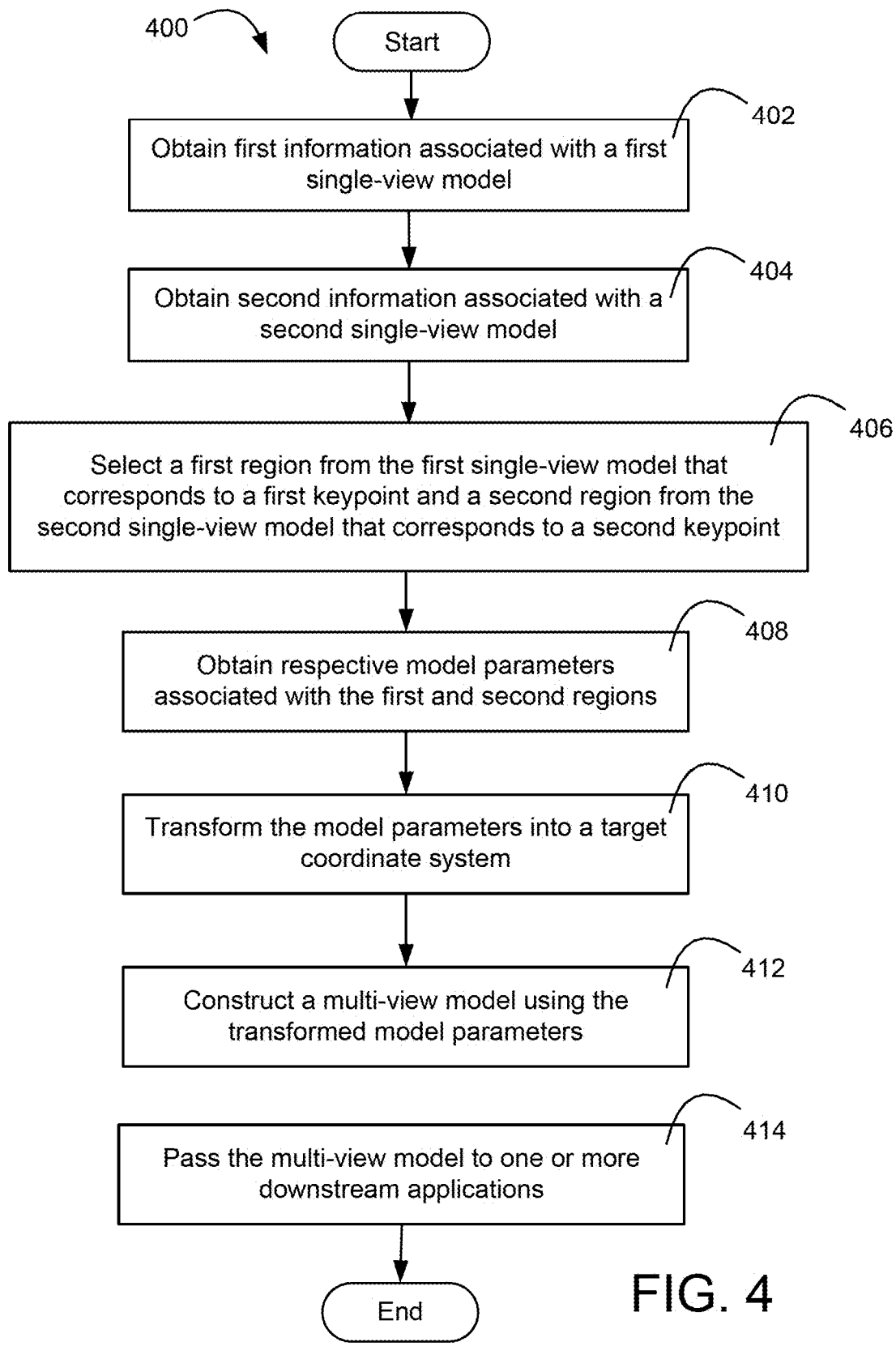
FIG. 4 is a flow diagram illustrating operations that may be associated with the construction of a multi-view human model.

FIG. 4 shows a flow diagram illustrating operations 400 that may be associated with the construction of a multi-view human model (e.g., the multi-view model 206 in FIG. 2). The operations may be performed by a multi-view model constructor such as the multi-view model construction 208 shown in FIG. 2. As shown, the multi-view model constructor may at 402 obtain (e.g., receive) first information associated with a first single-view model of a patient. The first information obtained by the multi-view model constructor may include, for example, parameters of the first single-view model (e.g., a plurality of vertices included in the first model), an indication of one or more keypoints covered by the first single-view model, and/or an indication of the respective levels of accuracy or confidence for the covered keypoints. At 404, the multi-view model constructor may obtain (e.g., receive) second information associated with a second single-view model of the patient. The second information received by the multi-view model constructor may include, for example, parameters of the second single-view model (e.g., a plurality of vertices included in the second model), an indication of one or more keypoints covered by the second single-view model, and/or an indication of the respective levels of accuracy or confidence for the covered keypoints. At 406, the multi-view model constructor may select, based on the first and/or second information, a first region (e.g., a first cuboid) of the first single-view model that is associated with a first keypoint (e.g., left shoulder) and a second region (e.g., a second cuboid) of the second single-view model that is associated with a second keypoint (e.g., right shoulder). The multi-view model constructor may select the first single-view model for the first region based on a determination that the first information indicates that the first single-view models covers the first keypoint with a satisfactory level of accuracy or confidence (e.g., the level of accuracy or confidence for the first keypoint exceeds a predetermined threshold). Similarly, the multi-view model constructor may select the second single-view model for the second region based on a determination that the second information indicates that the second single-view models covers the second keypoint with a satisfactory level of accuracy or confidence (e.g., the level of accuracy or confidence for the second keypoint exceeds the predetermined threshold).

At 408, the multi-view model constructor may obtain parameters from the first single-view model that are associated with the first region and parameters from the second single-view model that are associated with the second region. The parameters may include, for example, respective vertices of the first and second single-view models that correspond to the first and second regions. At 410, the multi-view model constructor may transform the vertices from the respective coordinate systems associated with the first and second single-view model (e.g., associated with first and second sensing devices that generate the single-view models) into a target coordinate system (e.g., a world coordinate system) associated with a target multi-view human model. At 412, the multi-view model constructor may generate the target multi-view human model using at least the transformed vertices of the first and second single-view models, before the passing the multi-view human model to a downstream application for use or display at 414.

For simplicity of explanation, the operations 400 of the multi-view model constructor are depicted and described herein with a specific order. It should be noted, however, that these operations may occur in various orders, concurrently, and/or with other operations not presented or described herein. Furthermore, it should also be noted that not all operations that the multi-view model constructor is capable of performing are depicted in FIG. 4 and described herein. It should also be noted that not all illustrated operations may be required to be performed by the multi-view model constructor.

Figure 5:
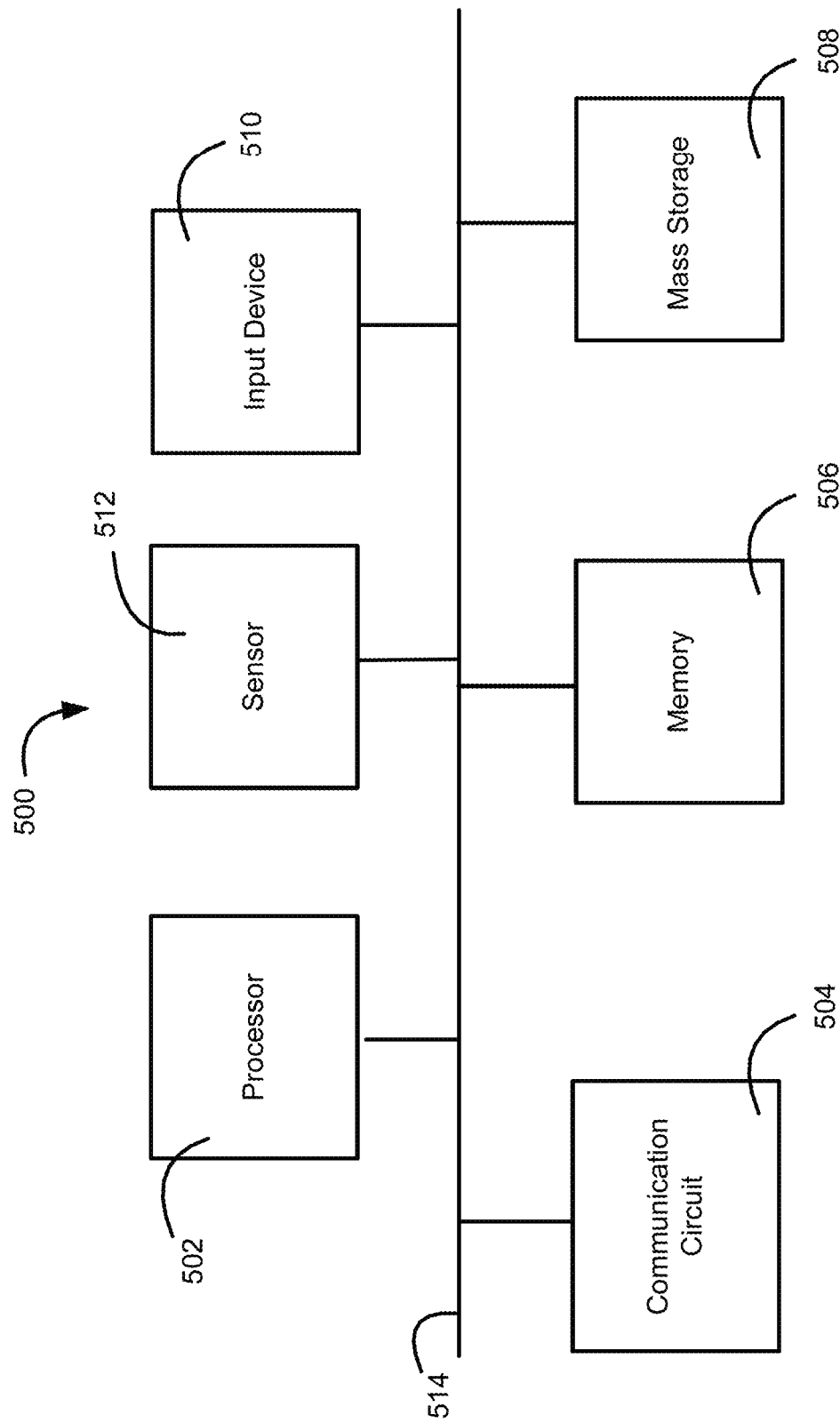
FIG. 5 is a block diagram illustrating an example apparatus that may be configured to perform the single-view and/or multi-view model construction operations described herein.

The systems, methods, and/or instrumentalities described herein may be implemented using one or more processors, one or more storage devices, one or more sensors, and/or other suitable accessory devices such as display devices, communication devices, input/output devices, etc. FIG. 5 is a block diagram illustrating an example apparatus 500 that may be configured to perform the single-view and/or multi-view model construction operations described herein. As shown, the apparatus 500 may include a processor (e.g., one or more processors) 502, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The apparatus 500 may further include a communication circuit 504, a memory 506, a mass storage device 508, an input device 510, a sensor 512, and/or a communication link 514 (e.g., a communication bus) over which the one or more components shown in the figure may exchange information.

The communication circuit 504 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 506 may include a storage medium (e.g., a non-transitory storage medium) configured to store machine-readable instructions that, when executed, cause the processor 502 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 508 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 502. The input device 510 may include a keyboard, a mouse, a voice-controlled input device, a touch sensitive input device (e.g., a touch screen), and/or the like for receiving user inputs to the apparatus 500. The sensor 512 may be included in the apparatus 500 if, for example, the apparatus 500 is configured to perform one or more image capturing functions as described herein (e.g., if the apparatus 500 is a sensing device as described herein). The sensor 512 may include a 2D visual sensor (e.g., a 2D camera), a 3D visual sensor (e.g., a 3D camera), an RGB sensor, a depth sensor, a RGB plus depth (RGB-D) sensor, a thermal sensors (e.g., an infrared (FIR) or near-infrared (NIR) sensor), a radar sensor, and/or other types of image capturing devices or circuitries.

It should be noted that the apparatus 1100 may operate as a standalone device or may be connected (e.g., networked or clustered) with other computation devices to perform the functions described herein. And even though only one instance of each component is shown in FIG. 11, a skilled person in the art will understand that the apparatus 1100 may include multiple instances of one or more of the components shown in the figure.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A method for constructing three-dimensional (3D) human models, the method comprising:
   obtaining a first 3D model of a human body present in a medical environment, wherein the first 3D model is determined based on at least a first image of the human body captured by a first sensing device installed in the medical environment;
   obtaining a second 3D model of the human body presented in the medical environment, wherein the second 3D model is determined based on at least a second image of the human body captured by a second sensing device installed in the medical environment;
   selecting a first region from the first 3D model based on a determination that the first region of the first 3D model covers a first keypoint of the human body and that the first keypoint is visible in the first image and invisible in the second image;
   selecting a second region from the second 3D model based on a determination that the second region of the second 3D model covers a second keypoint of the human body and that the second keypoint is visible in the second image and invisible in the first image; and
   generating a third 3D model of the human body based on at least the first region of the first 3D model and the second region of the second 3D model.

2. The method of claim 1, further comprising determining, based on the first 3D model, a first set of vertices associated with the first region of the first 3D model and determining, based on the second 3D model, a second set of vertices associated with the second region of the second 3D model, wherein the third 3D model of the human body is generated based on at least the first set of vertices and the second set of vertices.

3. The method of claim 2, further comprising:
   determining respective locations of the first set of vertices in a world coordinate system associated with the third 3D model based on respective locations of the first set of vertices in a first coordinate system associated with the first sensing device and an installation location of the first sensing device in the world coordinate system; and
   determining respective locations of the second set of vertices in the world coordinate system associated with the third 3D model based on respective locations of the second set of vertices in a second coordinate system associated with the second sensing device and an installation location of the second sensing device in the world coordinate system;
   wherein the third 3D model of the human body is generated based on at least the respective locations of the first set of vertices in the world coordinate system and the respective locations of the second set of vertices in the world coordinate system.

4. The method of claim 1, wherein the first 3D model, the second 3D model and the third 3D model of the human body indicate respective shapes and poses of the human body in the medical environment.

5. The method of claim 1, wherein the first region corresponds to a first cuboid in the first 3D model and the second region corresponds to a second cuboid in the second 3D model.

6. The method of claim 1, further comprising determining that the first 3D model covers the second a third keypoint of the human body with a first confidence level and that the second 3D model covers the third keypoint of the human body with a second confidence level, and selecting a third region that covers the third keypoint of the human body from the first 3D model based on a determination that the first confidence level is higher than the second confidence level, wherein the third 3D model of the human body is generated further based on the third region selected from the first 3D model.

7. The method of claim 1, further comprising receiving first information from the first sensing device that indicates whether the first keypoint is in the field of view of the first sensing device, and receiving second information from the second sensing device that indicates whether the second keypoint is in the field of view of the second sensing device.

8. The method of claim 1, wherein the method is implemented by the first sensing device or the second sensing device.

9. The method of claim 1, wherein the first 3D model is constructed by the first sensing device and the second 3D model is constructed by the second sensing device, and wherein the method further comprises receiving the first 3D model from the first sensing device.

10. An apparatus, comprising:
    one or more processors configured to:
    obtain a first 3D model of a human body presented in a medical environment, wherein the first 3D model is determined based on at least a first image of the human body captured by a first sensing device installed in the medical environment;
    obtain a second 3D model of the human body present in the medical environment,
    wherein the second 3D model is determined based on at least a second image of the human body captured by a second sensing device installed in the medical environment;
    select a first region from the first 3D model based on a determination that the first region of the first 3D model covers a first keypoint of the human body and that the first keypoint is visible in the first image and invisible in the second image;
    select a second region from the second 3D model based on a determination that the second region of the second 3D model covers a second keypoint of the human body and that the second keypoint is visible in the second image and invisible in the first image; and
    generate a third 3D model of the human body based on at least the first region of the first 3D model and the second region of the second 3D model.

11. The apparatus of claim 10, wherein the one or more processors are further configured to determine, based on the first 3D model, a first set of vertices associated with the first region of the first 3D model and determine, based on the second 3D model, a second set of vertices associated with the second region of the second 3D model, wherein the third 3D model of the human body is generated based on at least the first set of vertices and the second set of vertices.

12. The apparatus of claim 11, wherein the one or more processors are further configured to:
  determine respective locations of the first set of vertices in a world coordinate system associated with the third 3D model based on respective locations of the first set of vertices in a first coordinate system associated with the first sensing device and an installation location of the first sensing device in the world coordinate system; and
  determine respective locations of the second set of vertices in the world coordinate system associated with the third 3D model based on respective locations of the second set of vertices in a second coordinate system associated with the second sensing device and an installation location of the second sensing device in the world coordinate system;
  wherein the third 3D model of the human body is generated based on at least the respective locations of the first set of vertices in the world coordinate system and the respective locations of the second set of vertices in the world coordinate system.

13. The apparatus of claim 10, wherein the first 3D model, the second 3D model and the third 3D model of the human body indicate respective shapes and poses of the human body in the medical environment.

14. The apparatus of claim 10, wherein the first region corresponds to a first cuboid in the first 3D model and the second region corresponds to a second cuboid in the second 3D model.

15. The apparatus of claim 10, wherein the one or more processors are further configured to determine that the first 3D model covers a third keypoint of the human body with a first confidence level and that the second 3D model covers the third keypoint of the human body with a second confidence level, the one or more processors further configured to select a third region that covers the third keypoint of the human body from the first 3D model based on a determination that the first confidence level is higher than the second confidence level, wherein the third 3D model of the human body is generated further based on the third region selected from the first 3D model.

16. The apparatus of claim 10, wherein the one or more processors are further configured to receive first information from the first sensing device that indicates whether the first keypoint is in the field of view of the first sensing device, and receive second information from the second sensing device that indicates whether the second keypoint is in the field of view of the second sensing device.

17. The apparatus of claim 10, wherein the apparatus further comprises the first sensing device or the second sensing device.

18. The apparatus of claim 10, wherein the first 3D model is constructed by the first sensing device and the second 3D model is constructed by the second sensing device, and wherein the one or more processors are further configured to receive the first 3D model from the first sensing device and the second 3D model from the second sensing device.

* * * * *